United States Patent [19]
Cliffe et al.

[11] Patent Number: 5,585,374
[45] Date of Patent: Dec. 17, 1996

[54] AMIDE DERIVATIVES

[75] Inventors: Ian A. Cliffe, Slough; Alan C. White, Staines, both of England

[73] Assignee: John Wyeth Brother, Limited, Maidenhead, England

[21] Appl. No.: 379,579

[22] PCT Filed: Jul. 22, 1993

[86] PCT No.: PCT/GB93/01542

§ 371 Date: Feb. 1, 1995

§ 102(e) Date: Feb. 1, 1995

[87] PCT Pub. No.: WO94/03444

PCT Pub. Date: Feb. 12, 1994

[30] Foreign Application Priority Data

Aug. 5, 1992 [GB] United Kingdom .................. 9216649
Apr. 17, 1993 [GB] United Kingdom .................. 9307958

[51] Int. Cl.$^6$ .......................... A61K 31/44; A61K 31/55; C07D 401/04; C07D 401/10
[52] U.S. Cl. .......................... 514/212; 514/183; 514/326; 514/331; 514/339; 514/357; 514/428; 540/596; 540/597; 540/610; 546/205; 546/207; 546/208; 546/233; 546/234; 546/337; 546/277.7; 546/282.4; 546/268.1; 546/279.1; 546/194; 548/568; 548/950; 544/130; 544/131; 544/360; 544/364
[58] Field of Search ...................... 540/596, 597, 540/610; 546/207, 208, 202, 233, 234, 273, 337, 277.4; 548/568, 950; 514/212, 183, 326, 331, 339, 357, 428

[56] References Cited

U.S. PATENT DOCUMENTS

| | | | |
|---|---|---|---|
| 4,530,932 | 7/1985 | Uclaf ........................................ | 514/318 |
| 4,997,841 | 3/1991 | Glaxo Group Ltd. .................. | 514/323 |
| 5,066,660 | 11/1991 | Glaxo Group Ltd. .................. | 514/323 |
| 5,240,942 | 8/1993 | Adir et Compagnie ................ | 514/314 |
| 5,242,933 | 9/1993 | Adir et Compagnie ................ | 514/338 |
| 5,250,542 | 10/1993 | Cantrell et al. ........................ | 514/315 |
| 5,250,544 | 10/1993 | Adir et Compagnie ................ | 514/319 |
| 5,525,600 | 6/1996 | Baudy ..................................... | 514/212 |

FOREIGN PATENT DOCUMENTS

| | | | |
|---|---|---|---|
| 0112191 | 9/1983 | European Pat. Off. ...... | C07D 401/04 |
| 0303506 | 2/1989 | European Pat. Off. ...... | C07D 401/04 |
| 0466585 | 1/1992 | European Pat. Off. ...... | C07D 211/22 |
| 0481744 | 4/1992 | European Pat. Off. ...... | C07D 295/18 |
| 1106861 | 3/1968 | United Kingdom ........... | C07D 29/38 |
| 1114852 | 5/1968 | United Kingdom ........... | C07D 29/38 |
| 1319040 | 5/1973 | United Kingdom ........... | C07D 29/12 |
| 9206960 | 4/1992 | WIPO .......................... | C07D 213/56 |

OTHER PUBLICATIONS

J. Med. Chem., 12, 1969, pp. 940–941, Coutts et al.

*Primary Examiner*—Philip I. Datlow
*Attorney, Agent, or Firm*—Arthur G. Seifert

[57] ABSTRACT

Amide derivatives of formula (I) and their pharmaceutically acceptable salts (where a and b each represent 0, 1, 2 or 3 such that a+b=0, 1, 2 or 3, the dotted line represents an optional double bond, A is an optionally substituted $C_{1-2}$-alkylene chain, R is mono or bicyclic aryl or heteroaryl radical, $R^1$ is hydrogen or lower alkyl, $R^2$ is an aryl, aralkyl, heteroaryl or heteroarylalkyl and —$CONR^3R^4$ represents a specified amide group) are 5-HT$_{1A}$ binding agents and may be used, for example, as anxiolytics.

$$R \underset{(CH_2)_b}{\overset{(CH_2)_a}{\diagdown\!\!\!\diagup}} N-A-CR^1R^2.CONR^3R^4 \qquad (I)$$

11 Claims, No Drawings

AMIDE DERIVATIVES

This application is a 371 national stage application of international application PCT/GB93/01542, filed Jul. 22, 1993.

This invention relates to novel amide derivatives, to processes for their preparation, to their use and to pharmaceutical compositions containing them. The novel compounds act on the central nervous system by binding to 5-HT receptors (as more fully explained below) and hence can be used as medicaments for treating humans and other mammals. EP-A-0481744 discloses 2,3,4,5,6,7-hexahydro-1{4-[4-[1-[4-(2-methoxyphenyl)piperazinyl]]-2-phenylbutyryl}-1H-azepine and its salts that are 5-HT$_{1A}$ binding agents useful, for example, as anxiolytics. WO 92/06960 discloses other piperazinecarboxamides which are also useful as 5-HT$_{1A}$ binding agents. EP-A-0466585 discloses piperidine, tetrahydropyridine and pyrrolidine derivatives which are stated to have 5HT$_{1A}$ agonist or antagonist properties and useful in the treatment of hypertension, migraine, depression, anxiety, schizophrenia, stress and pain.

The novel compounds of the invention are those of general formula

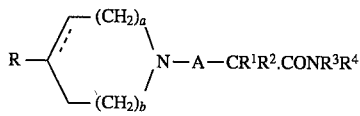

and the pharmaceutically acceptable acid addition salts thereof.

In formula I
a and b each represent 0,1,2 or 3 such that the sum of a+b is 0,1,2 or 3,
the dotted line represents an optional double bond which may be present in the ring, provided that a is at least 1,
A is an alkylene chain of 1 or 2 carbon atoms optionally substituted by one or more lower alkyl groups,
R is a mono or bicyclic aryl or heteroaryl radical,
$R^1$ is hydrogen or lower alkyl,
$R^2$ is an aryl, aryl (lower)alkyl, heteroaryl or heteroaryl (lower)alkyl radical,
$R^3$ is hydrogen or lower alkyl, $R^4$ is hydrogen, an alkyl group of 1 to 10 carbon atoms, cycloalkyl of 3 to 12 carbon atoms, cycloalkyl(lower)alkyl, aryl or aryl(lower)alkyl or
$R^3$ and $R^4$ together with the nitrogen atom to which they are both attached represent a saturated heterocyclic ring which may contain a further hetero atom [eg an azetidino, pyrrolidino, piperidino, hexahydroazepino, heptamethyleneimine, morpholino or piperazino ring which may be optionally substituted by, for example, lower alkyl, aryl, aryl(lower)alkyl), lower alkoxy, halogen or halo(lower)alkyl].

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl.

A cycloalkyl group can contain 3 to 12 carbon atoms. Preferably a cycloalkyl group is cyclopentyl, cyclohexyl or cycloheptyl, most preferably cyclohexyl. Cycloalkyl groups also include bicyclic, tricyclic and tetracyclic groups, eg adamantyl.

When used herein "aryl" means an aromatic radical having 6 to 12 carbon atoms (eg phenyl or naphthyl) which optionally may be substituted by one or more substituents. Preferred substituents are lower alkyl. lower alkoxy (eg methoxy, ethoxy, propoxy, butoxy), halogen, halo(lower) alkyl (eg trifluoromethyl), nitro, nitrile, amido, (lower) alkoxycarbonyl, amino, (lower)alkylamino or di(lower) alkylamino substituents. Two substituents on the aromatic ring may be connected together to form another ring system. For example R may be a bicyclic oxygen-containing radical of the formula

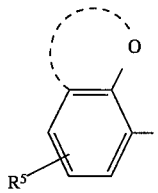

wherein $R^5$ represents hydrogen or one or more same or different substituents selected from lower alkyl, halogen, hydroxy, (lower)alkoxy, hydroxy(lower)alkyl, (lower) alkoxy(lower alkyl), lower alkanoyloxy(lower alkyl), (lower)alkylcarbonyl, (lower)alkylcarbonyl(lower)alkyl, (lower) alkylcarbonylamino, amino, (lower)alkylamino or di(lower) alkylamino and the heterocyclic ring containing the oxygen atom contains a total of 5 to 7 ring members, said heterocyclic ring being saturated or unsaturated, being optionally substituted (eg by one or more substituents $R^6$ where $R^6$ has the meaning given for $R^5$ above and optionally containing one or more hetero ring members (eg —O—, —S—, —SO$_2$— or —NR$^7$— where $R^7$ is hydrogen or lower alkyl) in addition to the oxygen atom illustrated A preferred example of such a bicyclic oxygen radical is a radical of the formula

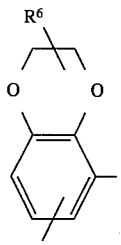

where $R^5$ and $R^6$ are as defined above; preferably $R^5$ and $R^6$ are both hydrogen.

The term "heteroaryl" refers to an aromatic radical containing one or more hetero atoms (eg oxygen, nitrogen, sulphur) and which may be optionally substituted by one or more substituents. Examples of suitable substituents are given above in connection with "aryl" radicals. The heteroaryl radical may, for example, contain up to 10 ring atoms. Preferably the heteroaryl radical is a monocyclic radical containing 5 to 7 ring atoms. Preferably the hetero ring contains a nitrogen hetero atom with or without one or more further hetero atoms.

When R is a heteroaryl radical it is preferably an optionally-substituted pyrimidyl (particularly 2-pyrimidyl), 1,2-benzisothiazolyl or indolyl [particularly indol-3-yl which may be optionally substituted eg by (lower)alkoxy for example in the 5-position] radical.

When $R^2$ is a heteroaryl or heteroaryl-lower alkyl the "heteroaryl" group is preferably a nitrogen containing heteroaryl radical (eg an optionally substituted pyridinyl, pyrimidinyl or pyrazinyl radical) or a heteroaryl radical containing an oxygen or sulphur atom as a hetero atom eg an optionally substituted thienyl or furyl group.

Preferred compounds of formula I have the characteristics either singly or in any possible combination:

(a) the ring system

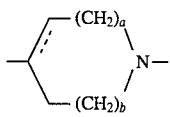

is

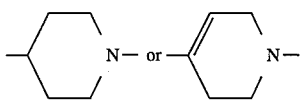

(b) R is an optionally substituted phenyl eg 2-(lower) alkoxyphenyl (for example 2-methoxyphenyl) or optionally substituted indolyl (eg 5-methoxy-1H-indol-3-yl)

(c) A is —$CH_2$— or —$CH_2.CH_2$—

(d) $R^1$ is hydrogen (e) $R^2$ is substituted or unsubstituted phenyl (f) $R^3$ is hydrogen and $R^4$ is tert.alkyl or cycloalkyl (eg cyclohexyl) or $R^3$ and $R^4$ together with the nitrogen atom to which they are both attached represent piperidino or hexahydroazepino.

A particularly preferred compound is (+)-2,3,4,5,6,7-hexahydro-1-(4-(1-(1,2,3,6-tetrahydro-4-(2-methoxyphenyl)pyridyl))-2-phenyl-butyryl)-1H-azepine.

The compounds of the invention may be prepared by methods known in the art from known starting or starting materials that may be prepared by conventional methods. One method comprises alkylation of a compound of formula

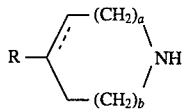 (II)

(where R, a, b and the dotted line are as defined above) with an alkylating agent providing the group

—A—$CR^1R^2.CONR^3R^4$ (III)

(where A, $R^1$, $R^2$, $R^3$ and $R^4$ have the meanings given above)

The alkylating agent may be, for example a compound of formula

X—A—$CR^1R^2CONR^3R^4$ (IV)

where A, $R^1$ $R^2$ $R^3$ and $R^4$ are as defined above and X is a leaving group such as halogen or an alkyl- or aryl-sulphonyloxy group. Alternatively the alkylating agent may be an unsaturated compound of formula $CH_2$=$CR^2CONR^3R^4$ (V)

(where $R^2$, $R^3$ and $R^4$ are as defined above) and the compound of formula (V) is reacted with the piperazine of formula (II) by means of a Michael reaction.

The starting compound of formula II may be prepared by known methods. The unsaturated compounds (ie compounds where the dotted line represents a double bond) may be prepared by dehydration of hydroxy compounds of formula

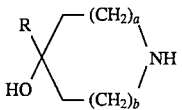 (VI)

In an alternative method of preparing the compounds of the invention an amine of formula $NHR^3R^4$ (VII)

(where $R^3$ and $R^4$ are as defined above) is acylated with an acid of formula

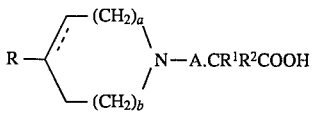 (VIII)

(where a, b, the dotted line, A, $R^1$ and $R^2$ are as defined above) or with an acylating derivative thereof. Examples of acylating derivatives include the acid halides (eg acid chlorides), azides, anhydrides, imidazolides (eg obtained from carbonyldiimidazole), activated esters or O-acyl ureas obtained from a carbodiimide such as a dialkylcarbodiimide particularly dicyclohexyl-carbodiimide. Preferably the amine is acylated with the acid by the use of a coupling agent such as 1,1'-carbonyldiimidazole, isobutylchloroformate or diphenylphosphinyl chloride.

The acids of formula (VIII) may be prepared by methods known in the art eg from the compounds of formula (II). For example a compound of formula (II) may be reacted with an acid of formula $CH_2$=$CR^2COOH$ by means of a Michael Reaction, or with an acid of formula X—A—$CR^1R^2COOH$ (where X, A, $R^1$ and $R^2$ have the meanings given above).

The compounds; of formula (I) where the dotted line represents a double bond may be prepared by dehydrating a hydroxy amide of formula

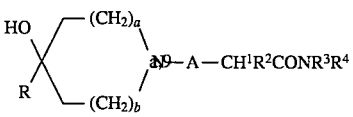 (IX)

(where a, b, A, R, $R^1$, $R^2$, $R^3$ and $R^4$ have the meanings given above).

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomeric forms. All steroisomeric forms are included within the invention. The compounds can be, for example, racemates or optically active forms. The optically active forms can be obtained by resolution of the racemates or by asymmetric synthesis. The compounds of the present invention possess pharmacological activity. In particular, they act on the central nervous system by binding to 5-HT receptors, particularly receptors of the $5\text{-HT}_{1A}$ type. In general, the compounds selectively bind to receptors of the $5\text{-HT}_{1A}$ type to a a much greater extent than they bind to other receptors such as $\alpha_1$. The compounds can be used for the treatment of CNS disorders, such as anxiety in mammals, particularly humans. They may also be useful as antidepressants, hypotensives and as agents for regulating the sleep/wake cycle, feeding behaviour and/or sexual function and as cognition enhancing agents.

The compounds of the invention are tested for 5-HT$_{1A}$ receptor binding activity in rat hippocampal membrane homogenate by the method of B S Alexander and M D Wood, J Pharm Pharmacol, 1988, 40, 888–891. In this procedure 2,3,4,5,6,7-hexahydro-1-(4-(1-(1,2,3,4,5,6-hexahydro-4-(2-methoxyphenyl)pyridyl))-2-phenyl butyryl)- 1H-azepine and its (+)-enantiomer, representative compounds of the invention, had IC$_{50}$ values respectively of 1.2 nM and 0.2 nM. The affinity for $\alpha_1$ sites (as measured by the procedure of A L Marrow et al. Mol Pharmacol, 1986, 29, 321) for the compounds were respectively IC$_{50}$=1080 nM and 250 nM.

The compounds are tested for 5-HT$_{1A}$ receptor antagonism activity in a test involving the antagonism of 5-carboxamidotryptamine in the guinea-pig ileum in vitro (based upon the procedure of Fozard et al, Br J Pharmac, 1985, 86, 601 P). The above mentioned representative compounds exhibit pA$_2$ values of respectively 9.1 and 9.0.

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, gildants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included. Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols (eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient: the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention

EXAMPLE 1

N-Cyclohexyl-3-(1-(1,2,3,6-tetrahydro-4-(5-methoxy-1H-indol-3-yl)pyridyl))-2-phenylpropanamide A stirred suspension of 5-methoxy-3-(1,2,3,6- tetrahydro-4-pyridinyl)-1H-indole (1.47 g, 6.4 mmol), N-cyclohexyl-2-phenylpropenamide (1.47 g, 6.4 mmol) and acetic acid (2 drops) in propanol (16 ml) was warmed to give a solution which was heated under reflux for 18 h, cooled to room temperature, and evaporated in vacuo. The residue was purified by chromatography (silica; ether→ethyl acetate) to give a solid. Recrystallisation from ethyl acetate gave the product free base as yellow crystals.

A hot solution of the crystals (1.38 g, 3.0 mmol) in ethanol (50 ml) was treated with oxalic acid dihydrate (0.38 g, 3.0 mmol), cooled to room temperature, and the precipitate filtered and washed with ethanol to give the oxalate salt of the product ( 1.52 g) as lemon crystals, m.p. 153°–160° (Found: C,69.3; H, 7.15; N, 8.25. C$_{29}$H$_{35}$N$_3$O$_2$. ½(CO$_2$H)$_2$. H$_2$O requires C, 69.2; H, 7.4; N, 8.1%).

EXAMPLE 2

3-(1-(1,2,3,4,5,6-hexahydro-4-(2-methoxyphenyl) pyridyl))-2-phenylpropionic acid A solution of 2-phenylpropenoic acid (1.17 g, 7.9 mmol) in isopropanol (5 ml) was treated with a solution of 1,2,3, 4,5,6-hexahydro-4-(2-methoxyphenyl)pyridine (1.03 g, 5.4 mmol) in isopropanol (7 ml), heated under reflux for 18 h. cooled to room temperature, and the precipitate filtered off and washed with isopropanol to give the product (120 g) m.p. 199°–200° C. (Found: C, 74.2; H, 7.6; N, 4.1. C$_{21}$H$_{25}$NO$_3$ requires, C, 74.3: H, 7.4; N, 4.1%).

EXAMPLE 3

1-(2-Chloroethyl)-1,2,3,4,5,6-hexahydro-4-(2-methoxyphenyl)pyridine

A solution of 1,2,3,4,5,6-hexahydro-4-(2-methoxyphenyl)pyridine hydrochloride (4.55 g, 20 mmol) in water (45 ml) was treated with ice and 5N aqueous sodium hydroxide (4 ml), and the mixture was extracted with dichloromethane (3×25 ml). The extracts were dried (Na$_2$SO$_4$) and concentrated in vacuo to give a viscous oil which solidified on standing. The oil was dissolved in dry dimethylformamide (20 ml), and N,N-diisopropylethylamine (5.2 ml, 30 mmol) and 1-bromo-2-chloroethane (1.8 ml, 22 mmol) were added. The solution was stirred under argon at room temperature for 18 h, poured into water (100 ml), extracted with ether (2×50 ml), and the extracts washed with water (50 ml), dried (Na$_2$SO$_4$) and concentrated in vacuo to give a yellow solid. Purification by chromatography (silica: ether) gave the product free base (1.34 g) as a white solid. The monohydrochloride salt was prepared in standard fashion, m.p. 216° C. (dec.) (Found: C,58.1; H, 7.5; N, 4.95 C$_{14}$H$_{20}$ClNO.HCl requires C,57.9; H, 7.3; N, 4.8%).

EXAMPLE 4

2,3,4,5,6,7-Hexahydro-1-(4-(1-(2,3,4,5,6-hexahydro-4-(2-methoxyphenyl)pyridyl))-2-phenylbutyryl)-1H-azepine Potassium bis(trimethylsilyl)amide (0.5 M in toluene: 11 ml, 5.5 mmol) was added dropwise, under argon maintaining the temperature below 5° C. to a stirred solution of 2,3,4,5,6,7-hexahydro-1-(phenylacetyl)-1H-azepine (1.14 g, 5.2 mmol) in dry toluene (5 ml). The suspension was stirred under argon at 0° C. for 1 h, and a solution of the product of Example 3 (1.34 g. 5.3 mmol) in dry toluene (7 ml) was added dropwise. The mixture was stirred under argon at 0° C. (warming to room temperature) for 65 h, treated with water (25 ml) and 2N aqueous sodium chloride (10 ml), the layers separated, and the aqueous phase extracted with ethyl acetate (2×25 ml). The combined organic phases were washed with water (50 ml) and concentrated in vacuo to give a yellow oil. The crude product was purified by chromatography [silica; ethyl acetate-hexane (2:3 to 1:0)] to give the free base of the product (0.39 g) which was dissolved in methanol (20 ml). The solution was acidified with ethereal hydrogen chloride (5 ml) and concentrated in vacuo to give a residue which upon trituration with ether gave the hydrochloride salt of the product (0.27 g) m.p. 154° C. (decomp) (Found: C,70.0; H, 8.6; N, 5.85. C$_{28}$H$_{38}$N$_2$O$_2$.HCl..0.5H$_2$O requires C, 70.05: H, 8.4; N, 5.8%).

The product was also prepared from the aminoacid of Example 2 and 2,3,4,5,6,7-hexahydro-1H-azepine by standard methods of amide formation.

EXAMPLE 5

(+)-2,3,4,5,6,7-Hexahydro-1-(4-(1-(1,2,3,4,5,6-hexahydro-4-(2-methoxyphenyl)pyridyl)-2-phenylbutyryl)-1H-azepine The racemic free base, from Example 4 was separated into its enantiomers by use of chiral h.p.l.c. with a Daicell "chiralcell OD" 21×250 mm preparative h.p.l.c. column [hexane - ethanol (98:2) and a flow rate of 9 ml/min]. U.V. Detection was at 254 nM.

The product free base was convened into the hydrochloride salt, m.p. 146°–147° C. (Found: C. 70.1; H, 8.4; N, 5.8. C$_{28}$H$_{38}$N$_2$O$_2$.HCl. ½H$_2$O requires C. 70.05; H, 8.4; N, 5.8%), $[\alpha]_D^{26}$+45° (MeOH).

We claim:
1. A compound of the formula

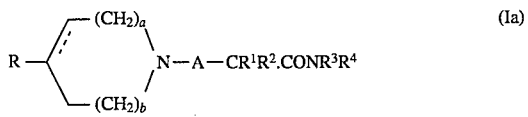

(Ia)

or a pharmaceutically acceptable acid addition salt thereof, wherein a and b each represent 0, 1 or 2 such that the sum of a+b is 1 or 2, the dotted line represents an optional double bond which may be present in the ring, provided that a is at least 1, A is an alkylene chain of 1 or 2 carbon atoms optionally substituted by one or more lower alkyl groups, R is aryl or heteroaryl, wherein aryl is phenyl or naphthyl each of which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, and heteroaryl is a monocyclic aromatic heterocyclic ring having 5 or 6 ring members or a bicyclic aromatic heterocyclic ring system having one or two aromatic heterocyclic rings with 5 or 6 members in each ring, and, as heteroatoms in either such monocyclic ring or bicyclic ring system, one or two N atoms or one N atom and one O or S atom, said N atoms being non-bridging, and which may be optionally substituted as for aryl, or R is a bicyclic oxygen-containing aryl radical of the formula

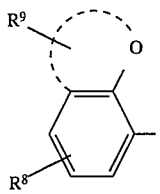

wherein the heterocyclic oxygen-containing ring has 5 to 7 ring members, said heterocyclic ring being non-aromatic and optionally having one further hetero ring member selected from —O— or —S—. where R$^8$ and R$^9$ represent hydrogen or one or more substituents independently selected from lower alkyl, halogen, hydroxy, loweralkoxy, hydroxyloweralkyl, loweralkoxyloweralkyl, loweralkanoyloxy(loweralkyl), loweralkylcarbonyl, loweralkylcarbonyl(loweralkyl), amino, loweralkylamino or di-loweralkylamino, R$^1$ is hydrogen or lower alkyl, R$^2$ is an aryl, aryl(lower)alkyl, heteroaryl or heteroaryl(lower)alkyl radical where aryl and heteroaryl are as defined for R above, R$^3$ is hydrogen or lower alkyl.

R$^4$ is hydrogen, an alkyl group of 1 to 10 carbon atoms, cycloalkyl of 3 to 12 carbon atoms, cycloalkyl(lower)alkyl, aryl or aryl(lower)alkyl where aryl and heteroaryl are as defied for R above or R$^3$ and R$^4$ together with the nitrogen atom to which they are both attached represent an azetidino, pyrrolidino, piperidino, hexahydroazepino, heptamethyleneimine, morpholino or piperazino ring which may be optionally substituted by one or more substituents independently selected from lower alkyl, axyl, aryl(lower)alkyl, lower alkoxy, halogen or halo(lower)alkyl where aryl is as defined for R above.

2. A compound as claimed in claim 1 in which R is an optionally substituted phenyl radical.

3. A compound as claimed in claim 1 in which A is —CH$_2$— or —CH$_2$CH$_2$—.

4. A compound as claimed in claim 1 in which R$^2$ is substituted or unsubstituted phenyl.

5. A compound as claimed in claim 1 in which R$^3$ is hydrogen and R$^4$ is tert. alkyl or cycloalkyl or R$^3$ and R$^4$ together with the nitrogen atom to which they are both attached represent piperidino or hexahydroazepino.

6. A compound as claimed in claim 1 which is N-cyclohexyl-3-(1-(1,2,3,6-tetrahydro-4-(5-methoxy-1H-indol-3-yl)pyridyl))-2-phenylpropanamide or 2,3,4,5,6,7-hexahydro-1-(4-(1-(1,2,3,4,5,6-hexahydro-4-(2-methoxyphenyl)pyridyl))-2-phenylbutyryl)-1H-azepine or (+)-2,3,4,5,6,7-hexahydro-1-(4-(1-(1,2,3,4,5,6-hexahydro-4-(2-methoxyphenyl)pyridyl))-2-phenyl-butyryl)-1H-azepine or a pharmaceutically acceptable acid addition salt thereof.

7. A pharmaceutical composition comprising a compound claimed in claim 1 in association with a pharmaceutically acceptable carrier.

8. A method of treating a mammal in need of 5-HT$_{1A}$ antagonism, comprising administering to such mammal an amount effective to provide 5-HT$_{1A}$ antagonism of a compound of the formula

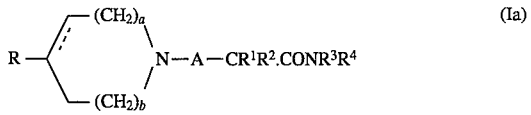

or a pharmaceutically acceptable acid addition salt thereof, wherein a and b each represent 0, 1 or 2 such that the sum of a +b is 1 or 2, the dotted line represents an optional double bond which may be present in the ring, provided that a is at least 1, A is an alkylene chain of 1 or 2 carbon atoms optionally substituted by one or more lower alkyl groups, R is aryl or heteroaryl, wherein aryl is phenyl or naphthyl each of which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, and heteroaryl is a monocyclic aromatic heterocyclic ring having 5 or 6 ring members or a bicyclic aromatic heterocyclic ring system having one or two aromatic heterocyclic rings with 5 or 6 members in each ring, and, as heteroatoms in either such monocyclic ring or bicyclic ring system, one or two N atoms or one N atom and one O or S atom, said N atoms being non-bridging, and which may be optionally substituted as for aryl, or R is a bicyclic oxygen-containing aryl radical of the formula

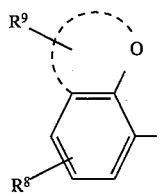

wherein the heterocyclic oxygen-containing ring has 5 to 7 ring members, said heterocyclic ring being non-aromatic and optionally having one further hereto ring member selected from —O— or —S—, where R$^8$ and R$^9$ represent hydrogen or one or more substituents independently selected from lower alkyl, halogen, hydroxy, loweralkoxy, hydroxyloweralkyl, loweralkoxyloweralkyl, loweralkanoyloxy(loweralkyl), loweralkylcarbonyl, loweralkylcarbonyl(loweralkyl), amine, loweralkylamino or di-loweralkylamino, R$^1$ is hydrogen or lower alkyl, R$^2$ is an aryl, aryl(lower)alkyl, heteroaryl or heteroaryl(lower)alkyl radical where aryl and heteroaryl are as defined for R above, R$^3$ is hydrogen or lower alkyl, R$^4$ is hydrogen, an alkyl group of 1 to 10 carbon atoms, cycloalkyl of 3 to 12 carbon atoms, cycloalkyl(lower)alkyl, aryl or aryl(lower)alkyl where aryl and heteroaryl are as defined for R above or R$^3$ and R$^4$ together with the nitrogen atom to which they are both attached represent an azetidino, pyrrolidino, piperidino, hexahydroazepino, heptamethyleneimine, morpholino or piperazino ring which may be optionally substituted by one or more substituents independently selected from lower alkyl, aryl, aryl(lower)alkyl, lower alkoxy, halogen or halo(lower)alkyl where aryl is as defined for R above.

9. A method of treatment according to claim 8 wherein the compound of formula Ia is N-cyclohexyl-3-(1-(1,2,3,6-tetrahydro-4-(5-methoxy-1H-indol-3-yl)pyridyl)-2-phenylpropanamide or 2,3,4,5,6,7-hexahydro-1-(4-(1-(1,2,3,6-hexahydro-4-(2-methoxyphenyl)pyridyl))-2-phenylbutyryl)-1H-azepine or (+)-2,3,4,5,6,7-hexahydro-1-(4-(1-(1,2,3,4,5,6-hexahydro-4-(2-methoxyphenyl)pyridyl))-2-phenyl-butyryl)-1H-azepine or a pharmaceutically acceptable acid addition salt thereof.

10. A method of treating a mammal suffering from anxiety, depression or a cognition disorder, comprising administering to such mammal an mount effective to alleviate such depression, anxiety or cognition disorder of a compound of the formula

or a pharmaceutically acceptable acid addition salt thereof, wherein a and b each represent 0, 1 or 2 such that the sum of a+b is 1 or 2, the dotted line represents an optional double bond which may be present in the ring, provided that a is at least 1, A is an alkylene chain of 1 or 2 carbon atoms optionally substituted by one or more lower alkyl groups, R is aryl or heteroaryl, wherein aryl is phenyl or naphthyl each of which may be optionally substituted by one or more substituents independently selected from lower alkyl, lower alkoxy, halogen, haloloweralkyl, nitro, nitrile, aminocarbonyl, loweralkoxycarbonyl, amino, loweralkylamino, or di-loweralkylamino, and heteroaryl is a monocyclic aromatic heterocyclic ring having 5 or 6 ring member or a bicyclic aromatic heterocyclic ring system having one or two aromatic heterocyclic rings with 5 or 6 members in each ring, and, as heteroatoms in either such monocyclic ring or bicyclic ring system, one or two N atoms or one N atom and one O or S atom, said N atoms being non-bridging, and which may be optionally substituted as for aryl, or R is a bicyclic oxygen-containing aryl radical of the formula

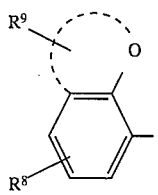

wherein the heterocyclic oxygen-containing ring has 5 to 7 ring members, said heterocyclic ring being non-aromatic and optionally having one further hetero ring member selected from —O— or —S—, where $R^8$ and $R^9$ represent hydrogen or one or more substituents independently selected from lower alkyl, halogen, hydroxy, loweralkoxy, hydroxyloweralkyl, loweralkoxyloweralkyl, loweralkanoyloxy(loweralkyl), loweralkylcarbonyl, loweralkylcarbonyl(loweralkyl), amino, loweralkylamino or di-loweralkylamino, $R^1$ is hydrogen or lower alkyl, $R^2$ is an aryl, axyl(lower)alkyl, heteroaryl or heteroaryl-(lower)alkyl radical where aryl and heteroaryl are as defined for R above, $R^3$ is hydrogen or lower alkyl, $R^4$ is hydrogen, an alkyl group of 1 to 10 carbon atoms, cycloalkyl of 3 to 12 carbon atoms, cycloalkyl(lower)alkyl, aryl or aryl(lower)alkyl where aryl and heteroaryl are as defined for R above or $R^3$ and $R^4$ together with the nitrogen atom to which they are both attached represent an azetidino, pyrrolidino, piperidino, hexahydroazepino, heptamethyleneimine, morpholino or piperazino ring which may be optionally substituted by one or more substituents independently selected from lower alkyl, aryl, aryl(lower)alkyl, lower alkoxy, halogen or halo(lower)alkyl where aryl is as defined for R above.

11. A method of treatment according to claim 10 wherein the compound of formula Ia is N-cyclohexyl-3-(1-(1,2,3,6-tetrahydro-4-(5-methoxy-1H-indol-3-yl)pyridyl))-2-phenyl-propanamide or 2,3,4,5,6,7-hexahydro-1-(4-(1-(1,2,3,4,5,6-hexahydro-4-(2-methoxyphenyl)pyridyl)-2-phenylbutyryl)-1H-azepine or (+)-2,3,4,5,6,7-hexahydro-1-(4-(1-(1,2,3,6-tetrahydro-4-(2-methoxyphenyl)pyridyl))-2-phenyl-butyryl)-1H-azepine or a pharmaceutically acceptable add addition salt thereof.

\* \* \* \* \*